(12) United States Patent
Ardanese et al.

(10) Patent No.: US 11,982,660 B2
(45) Date of Patent: May 14, 2024

(54) QUALITY CONTROL SYSTEM FOR ANALYZING THE QUALITY OF A BATTERY CELL THROUGH ANALYSIS OF A PHYSICAL PROPERTY OF A GAS FORMED DURING A CELL FORMATION PROCESS AND A METHOD OF ANALYZING THE SAME

(71) Applicant: GM Global Technology Operations LLC, Detroit, MI (US)

(72) Inventors: Raffaello Ardanese, Bloomfield Hills, MI (US); James R. Salvador, East Lansing, MI (US); Ryan Curtis Sekol, Grosse Pointe Woods, MI (US); Thomas A. Yersak, Royal Oak, MI (US); Dmitriy Bruder, Clinton Township, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 553 days.

(21) Appl. No.: 17/350,650

(22) Filed: Jun. 17, 2021

(65) Prior Publication Data
US 2022/0404325 A1    Dec. 22, 2022

(51) Int. Cl.
*G01N 33/00* (2006.01)
*G01N 7/00* (2006.01)
(Continued)

(52) U.S. Cl.
CPC .......... *G01N 33/0062* (2013.01); *G01N 7/00* (2013.01); *G01N 33/0036* (2013.01);
(Continued)

(58) Field of Classification Search
CPC .. G01N 33/0062; G01N 7/00; G01N 33/0036; H01M 10/4285; H01M 50/10;
(Continued)

(56) References Cited

U.S. PATENT DOCUMENTS 10,014,561 B2    7/2018  Sood et al.
2013/0260192 A1  10/2013 LePort
(Continued)

FOREIGN PATENT DOCUMENTS

CN    103344920 B    5/2016
CN    211528633 U    9/2020
(Continued)

OTHER PUBLICATIONS

KR-20220147253-A English Translation (Year: 2022).*
WO-2020110328-A1 English Translation (Year: 2020).*

*Primary Examiner* — Ryan D Walsh
(74) *Attorney, Agent, or Firm* — Vivacqua Crane, PLLC

(57) ABSTRACT

A quality control system analyzes the quality of a battery cell, with the battery cell defining a gas pouch configured to be filled with a gas. The quality control system includes a computational system including a processor and a memory, a manifold defining a passageway extending between an inlet port for receiving the gas and an outlet port, and at least one sensor in electronic communication with the computational system. The sensor is arranged to measure a physical property of the gas and transmit a signal to the computational system corresponding to the physical property of the gas. The computational system analyzes the physical property of the gas, accesses a threshold value corresponding to the physical property, compares the physical property to the threshold value, and assess a quality score for the battery cell. A corresponding method analyzes the quality of the battery cell with the quality control system.

20 Claims, 5 Drawing Sheets

(51) Int. Cl.
G01R 31/3832 (2019.01)
G01R 31/392 (2019.01)
H01M 10/42 (2006.01)
H01M 50/10 (2021.01)
H01M 50/105 (2021.01)

(52) U.S. Cl.
CPC ....... *H01M 10/4285* (2013.01); *H01M 50/10* (2021.01); *H01M 50/105* (2021.01); *G01R 31/3832* (2019.01); *G01R 31/392* (2019.01); *H01M 2220/20* (2013.01)

(58) Field of Classification Search
CPC ............ H01M 50/105; H01M 2220/20; G01R 31/3832; G01R 31/392
See application file for complete search history.

(56) References Cited

U.S. PATENT DOCUMENTS

| | | | |
|---|---|---|---|
| 2014/0089692 A1* | 3/2014 | Hanafusa | H02J 13/00022 713/310 |
| 2014/0266060 A1 | 9/2014 | Mng | |
| 2015/0303723 A1 | 10/2015 | Raghavan et al. | |
| 2017/0069889 A1* | 3/2017 | Yang | H01M 10/48 |
| 2018/0040926 A1* | 2/2018 | Keser | H01M 10/0436 |
| 2020/0292622 A1 | 9/2020 | Wu et al. | |
| 2020/0358147 A1 | 11/2020 | Dou et al. | |
| 2022/0102806 A1* | 3/2022 | Min | H01M 10/488 |
| 2022/0123559 A1 | 4/2022 | Stefanopoulou et al. | |
| 2022/0399592 A1* | 12/2022 | Schreiber | H01M 10/613 |
| 2022/0404186 A1 | 12/2022 | Bruder | |
| 2022/0404325 A1 | 12/2022 | Ardanese | |
| 2022/0404431 A1 | 12/2022 | Salvador | |
| 2023/0040106 A1* | 2/2023 | Youn | H01M 10/425 |
| 2023/0244200 A1 | 8/2023 | Charles et al. | |

FOREIGN PATENT DOCUMENTS

| | | |
|---|---|---|
| JP | 2012129023 A | 7/2012 |
| JP | 2014127341 A | 7/2014 |
| KR | 20220147253 A * | 11/2022 |
| WO | WO-2020110328 A1 * | 6/2020 |

\* cited by examiner

ND A METHOD OF ANALYZING THE
QUALITY CONTROL SYSTEM FOR ANALYZING THE QUALITY OF A BATTERY CELL THROUGH ANALYSIS OF A PHYSICAL PROPERTY OF A GAS FORMED DURING A CELL FORMATION PROCESS AND A METHOD OF ANALYZING THE SAME

INTRODUCTION

The present disclosure relates to a quality control system for analyzing the quality of a battery cell, and more particularly to a quality control system for analyzing the quality of a battery cell through analysis of a physical property of a gas formed during a cell formation process, and a method of analyzing the same.

In recent years, the use of electric motors to power vehicles has increased exponentially. To power the electric motors, battery packs comprised of numerous battery cells are utilized. Most battery cells can maintain a charge suitable to power the vehicle over a range of several hundred miles. However, occasionally battery cells are produced of low-quality that are unable to hold a sufficient charge. A common reason for a low-quality battery cell is an insufficient Solid Electrolyte Interphase (SEI) deposited on the anode of the battery cell. The SEI is formed by the reduction of electrolyte solvents, additives, and salts.

Current practices to analyze the quality of battery cells includes performing a discharge capacity check (i.e., checking that the cell provides capacity (measured in amp-hours) that is within a determined specification) and performing an inventory hold and open circuit voltage ("OCV") monitoring (which involves holding the inventory and checking for a decrease in OCV over time). While effective, such quality control measures are time intensive (with the potential for large quality spills and the added cost of overhead to store inventory) and data poor (i.e., not diagnostic or prognostic). Other methods of analyzing the quality of battery cells involve analyzing the SEI on the anode. However, the battery cell must be cut open (destroying the battery cell) to analyze the SEI.

Thus, while current quality control systems for analyzing the quality of a battery cell achieve their intended purpose, there is a need for a new and improved quality control system that addresses these issues.

SUMMARY

According to several aspects of the present disclosure, a quality control system analyzes the quality of a battery cell, with the battery cell defining a gas pouch configured to be filled with a gas formed during a cell formation process of the battery cell. The quality control system comprises a computational system comprising a processor and a memory. The quality control system further comprises a manifold defining a passageway extending between an inlet port configured to be in fluid communication with the gas pouch for receiving the gas and an outlet port in fluid communication with the inlet port through the passageway and configured to exhaust the gas from the manifold. The quality control system further comprises at least one sensor coupled to the manifold and in fluid communication with the passageway, with the sensor in electronic communication with the computational system, and with the sensor arranged to measure a physical property of the gas removed from the gas pouch and transmit a signal to the computational system corresponding to the physical property of the gas. The computational system is arranged to analyze the physical property of the gas with the processor and access a threshold value corresponding to the physical property stored in the memory to compare the physical property to the threshold value and assess a quality score for the battery cell.

In one aspect, the at least one sensor is further defined as a plurality of sensors comprising at least a pressure sensor configured to measure the pressure of the gas in the manifold and a temperature sensor configured to measure the temperature of the gas in the manifold, wherein the pressure sensor transmits the signal with the pressure of the gas to the computational system and the temperature sensor transmits the signal with the temperature of the gas to the computational system.

In another aspect, the computational system is arranged to analyze the pressure and temperature of the gas to determine a volume of the gas within the gas pouch, with the threshold value further defined as a volume threshold value and with the processor arranged to compare the volume to the volume threshold value and assess the quality score for the battery cell.

In another aspect, the volume threshold value is further defined as two volume threshold values, with one of the volume threshold values about 0.5 mL/Ah and the other one of the volume threshold values about 3 mL/Ah, with the quality score further defined as a low-quality score when the volume is below 0.5 mL/Ah or above 3 mL/Ah.

In another aspect, the plurality of sensors further comprises a gas detection sensor configured to measure the composition of the gas within the gas pouch and wherein the gas detection sensor transmits the signal with the composition of the gas to the computational system.

In another aspect, the threshold value is further defined as a composition threshold value and with the processor arranged to compare the composition of the gas to the composition threshold value and assess the quality score for the battery cell.

In another aspect, the quality score further defined as a low-quality score when the composition of the gas is above the composition threshold value.

In another aspect, the plurality of sensors comprises a plurality of the gas detection sensor, with each gas detection sensor configured to measure the composition of a different substance within the gas.

In another aspect, the composition threshold value is further defined as a cumulative composition threshold value and wherein the processor is arranged to summate the compositions of the different substances within the gas into a cumulative composition, compare the cumulative composition of the gas to the cumulative composition threshold value, and assess the quality score for the battery cell.

In another aspect, the gas detection sensor comprises one of a metal oxide sensor, an oxygen and nitrogen oxide (O2/NOx) sensor, and a hydrogen (H2) sensor.

In another aspect, the processor compares the quality score of the battery cell from the volume of the gas to the quality score of the battery cell from the composition of the gas and assess a global quality score for the battery cell.

According to several aspects of the present disclosure, a method of analyzing the quality of a battery cell with a quality control system is disclosed. The battery cell defines a gas pouch filled with a gas formed during a cell formation process of the battery cell. The quality control system comprises a computational system and a manifold defining a passageway extending between an inlet port configured to be in fluid communication with the gas pouch for receiving the gas and an outlet port in fluid communication with the inlet port through the passageway and configured to exhaust the gas from the manifold. The quality control system further comprises at least one sensor coupled to the manifold and in fluid communication with the passageway, with the sensor in electronic communication with the computational system. The method comprises flowing the gas from the gas pouch through the inlet port, through the passageway, across the at least one sensor, and through the outlet port, measuring a physical property of the gas with the at least one sensor, and transmitting a signal from the at least one sensor to a processor of the computational system corresponding to the physical property of the gas. The method further comprises analyzing the physical property of the gas with the processor, accessing a threshold value corresponding to the physical property stored in a memory of the computational system with the processor, comparing the physical property of the gas to the threshold value with the processor, and assessing a quality score for the battery cell with the processor.

In one aspect, the at least one sensor is further defined as a plurality of sensors comprising at least a pressure sensor configured to measure the pressure of the gas in the manifold and a temperature sensor configured to measure the temperature of the gas in the manifold. Measuring the physical property of the gas with the at least one sensor is further defined as measuring the pressure of the gas within the manifold with the pressure sensor and measuring the temperature of the gas within the manifold with the temperature sensor.

In another aspect, analyzing the physical property of the gas with the computational system is further defined as analyzing the pressure and temperature of the gas and determining a volume of the gas within the gas pouch with the processor.

In another aspect, the threshold value is further defined as a volume threshold value, with comparing the physical property of the gas to the threshold value with the processor further defined as comparing the volume of the gas to the volume threshold value and assessing the quality score for the battery cell with the processor further defined as assessing the quality score from the volume of the gas for the battery cell.

In another aspect, the volume threshold value is defined as two volume threshold values, with one of the volume threshold values about 0.5 mL/Ah and the other one of the volume threshold values about 3 mL/Ah and wherein the quality score is a low-quality score for the volume below 0.5 mL/Ah or above 3 mL/Ah.

In another aspect, the plurality of sensors further comprises a gas detection sensor and the method further comprises measuring the composition of the gas within the gas pouch with the gas detection sensor and transmitting a signal from the at least one sensor to the processor of the computational system corresponding to the composition of the gas.

In another aspect, the threshold value is further defined as a composition threshold value and the method further comprises comparing the composition of the gas to the composition threshold value and assessing a quality score from the composition of the gas for the battery cell.

In another aspect, the method further comprises assessing a global quality score from the quality score of the battery cell from the volume of the gas and the quality score of the battery cell from the composition of the gas.

According to several aspects of the present disclosure, a method of analyzing the quality of a battery cell with a quality control system is disclosed. The battery cell defines a gas pouch filled with a gas formed during a cell formation process of the battery cell. The quality control system comprises a computational system, a manifold defining a passageway extending between an inlet port and an outlet port, and a plurality of sensors coupled to the manifold and in fluid communication with the passageway. The sensors are in electronic communication with the computational system. The plurality of sensors comprise a pressure sensor, a temperature sensor, and a gas detection sensor. The method comprises flowing the gas from the gas pouch through the inlet port, through the passageway, across the sensors, and through the outlet port, measuring the pressure of the gas within the manifold with the pressure sensor, and measuring the temperature of the gas within the manifold with the temperature sensor. The method further comprises transmitting a signal from the at least one sensor to a processor of the computational system corresponding to the physical property of the gas, analyzing the pressure and temperature of the gas and determining a volume of the gas within the gas pouch with the processor, and accessing a volume threshold value, corresponding to the volume determined from the pressure and the temperature, stored in a memory of the computational system with the processor, the method further comprises comparing the volume of the gas to the volume threshold value with the processor, assessing a quality score from the volume of the gas for the battery cell with the processor, measuring the composition of the gas within the gas pouch with the gas detection sensor, and transmitting a signal from the at least one sensor to the processor of the computational system corresponding to the composition of the gas. The method further comprises accessing a composition threshold value stored in a memory of the computational system with the processor, comparing the composition of the gas to the composition threshold value with the processor, assessing a quality score from the composition of the gas for the battery cell with the processor, and assessing a global quality score from the quality score of the battery cell from the volume of the gas and the quality score of the battery cell from the composition of the gas.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
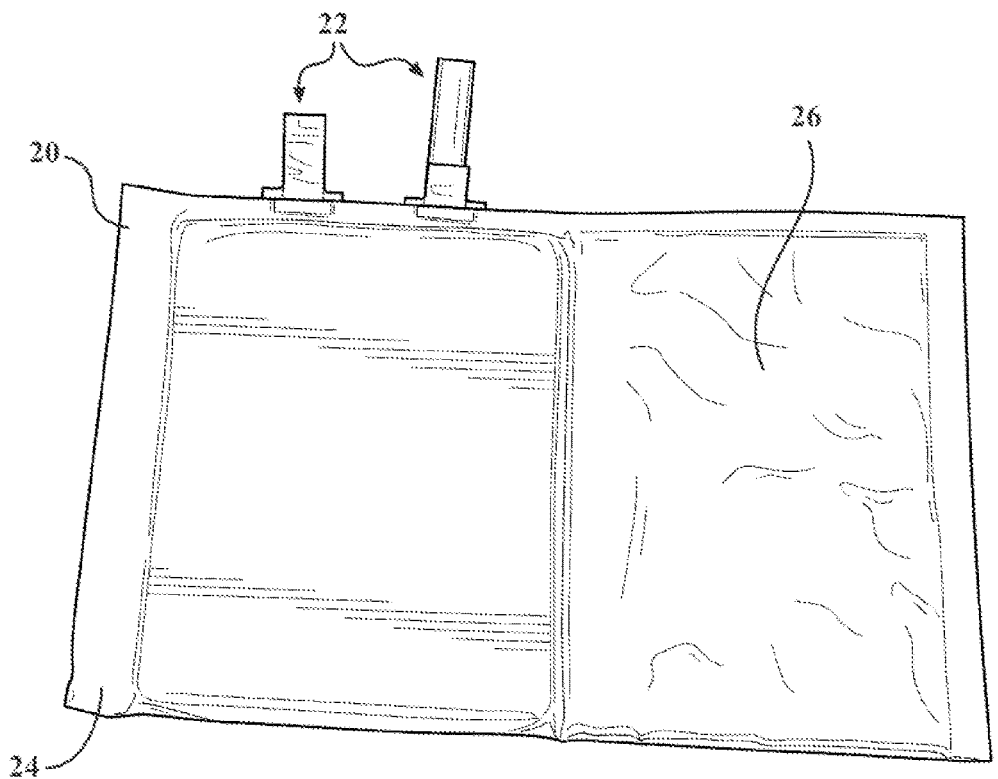
FIG. 1 is a perspective view of one example of a battery cell comprising a gas pouch, with the gas pouch in a deflated configuration.
Figure 2:
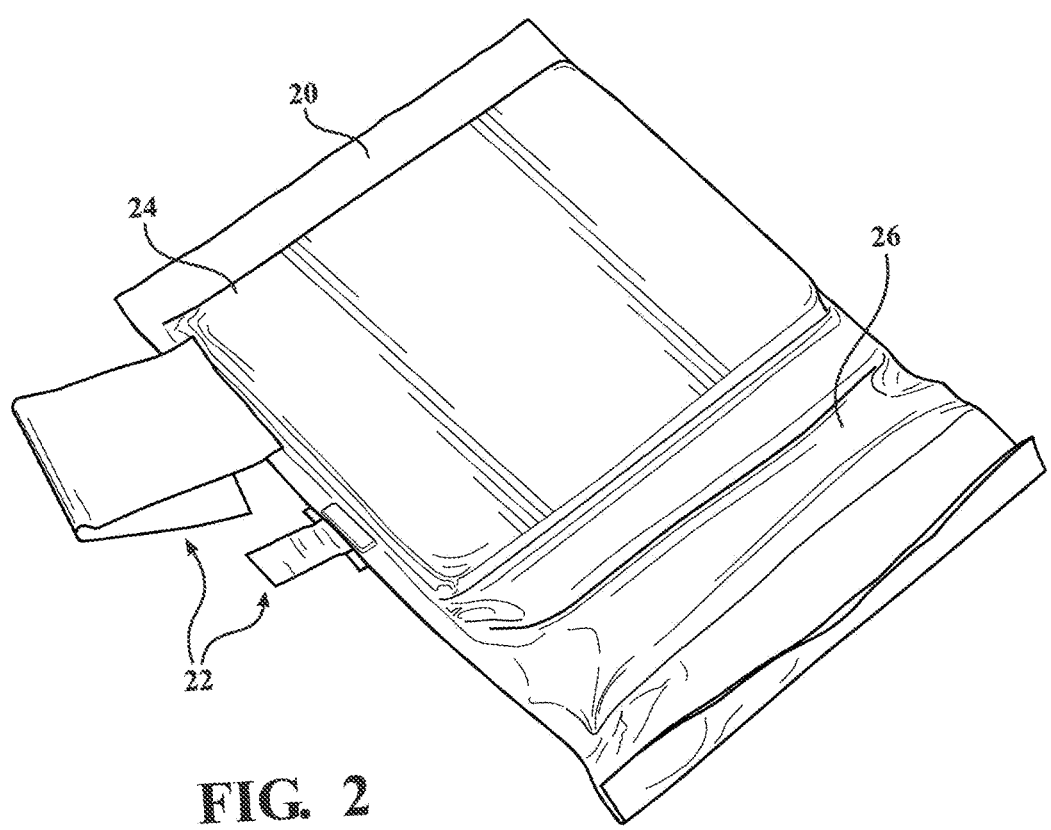
FIG. 2 is a perspective view of the battery cell shown in FIG. 1, with the gas pouch in an inflated configuration.

Referring to FIGS. 1 and 2, according to several aspects of the present disclosure, a battery cell is shown generally at 20. The battery cell 20 is a component of a battery pack. More specifically, the battery pack comprises multiple battery cells 20 that are electrically connected. The common application for such battery cells 20 is in an electric automotive vehicle. However, the battery cells 20 may be utilized in many other applications, such as non-automotive vehicular applications, consumer electronics, etc. The battery cell 20 disclosed herein is a lithium-ion battery cell. The battery cell comprises an electrolyte (not shown) and a pair of electrodes 22 that include an anode and a cathode. The cathode may NCM, NCMA, LMO, LFP, combinations thereof or any like material. The anode may comprise graphite, SiOx, Si, combinations thereof or any like material. The electrolyte may be carbonate based with a fluorinated Li salt. However, battery cells of different chemistries may be utilized.

The battery cell 20 disclosed herein may undergo numerous steps to produce the active battery cell 20. Although steps may vary between different types of battery cells, the battery cell 20 shown herein is produced by first preparing an electrode slurry (not shown) of active material, binder, and conductive agents that are mixed in specific mass ratios. Next, the electrode slurry is coated on the collectors and dried. During a calendering process, the porous electrodes 22 are compressed by driving the electrodes 22 through rollers (not shown). The electrodes 22 are then cut or punched into strips that are wound or stacked together with a separator (not shown). The electrodes 22 (comprising an anode and a cathode) are then placed in a sleeve 24 (more specifically, within a cavity defined by the sleeve 24). During a cell formation process, an electrolyte is injected into the cavity. The electrolyte permeates and fills pores within the electrodes 22. A charge is then applied to the electrodes 22 by first applying a constant current to a predetermined first voltage limit, then applying a second constant current to a second voltage limit, and then holding the voltage at the second voltage limit for a predetermined length of time. When the current is applied, the voltage is left to drift according to the charge states of the anode and the cathode. During the cell formation process, a Solid Electrolyte Interphase (SEI) is generated on the anode. The SEI (not shown) is formed by the reduction of electrolyte solvents, additives, and salts. The reduction of electrolyte occurs at characteristic voltages and is accompanied by production of gasses which must be vented from the cavity. To this end, the battery cell 20, as shown in FIGS. 1 and 2, further comprises a gas pouch 26 in fluid communication with the cavity. The gas pouch 26 is configured to expand from a deflated configuration to an inflated configuration when filled with the gas formed during the cell formation process of the battery cell 20.

Current practices to analyze the quality of battery cells involves performing a discharge capacity check (i.e., checking that the cell provides capacity (measured in amp-hours) that is within a determined specification) or performing an inventory hold and open circuit voltage ("OCV") monitoring (which involves holding the inventory and checking for a decrease in OCV over time). While effective, such quality control measures are time intensive (with the potential for large quality spills and the added cost of overhead to store inventory) and data poor (i.e., not diagnostic or prognostic).

However, the gas produced by the cell formation process provides data that be used to assess the quality of the battery cell 20. The excessive production of gas can be indicative of a low-quality battery cell 20. More specifically, in one example the battery cell 20 is expected to produce between 0.5-3 mL/Ah of gas. If the amount of gas produced is greater than 3 mL/Ah, the battery cell 20 may be low-quality. The excessive gas may be due to several reasons. As one example, the complete inactivity of electrolyte additives such as vinyl carbonate ("VC"), vinyl ethylene carbonate ("VEC"), etc. will lead to excessive consumption of ethylene carbonate ("EC") resulting gas production. In this situation, these battery cells 20 show very poor charge retention with cycling. Poor additive performance due to partial expiration and degradation will also lead to excessive EC consumption and increased gas generation volume though not to the extent as seen in the previous example.

In general, small gas volume results in the highest initial charge capacity of the battery cell 20, while an increase in gas volume (due to EC reduction) is correlated to degradation of charge capacity over time. Excessive Ethylene Carbonate (EC) reduction during the formation cycle consumes lithium salt in the electrolyte, which lowers the total available "lithium inventory" in the battery cell 20, which reduces ultimate charge capacity. Poor electrolyte additive performance causes a more rapid breakdown of the SEI layer. As a result, additional EC reduction is necessary to maintain the SEI layer. The SEI layer formed primarily from EC reduction has poor mechanical properties and greater thickness, which is inferior to one formed when electrolyte additives are present.

Furthermore, the composition of the gas provides data that can be used to assess the quality of the battery cell 20. For example, certain substances are consistently found in the gas pouch 26 after the cell formation process. Those substances include methane, ethene, ethane, butane, hydrogen, carbon monoxide, and carbon dioxide. The individual compositions of those substances may be indicative of quality defects during the cell formation process, such as no additives, humidity, aged electrolyte, and lean electrolyte. Furthermore, the cumulative amount of the substances may be greater than a threshold and indicative of a low-quality battery cell. The analysis of the composition of the gas will be described in greater detail below.

Figure 3:
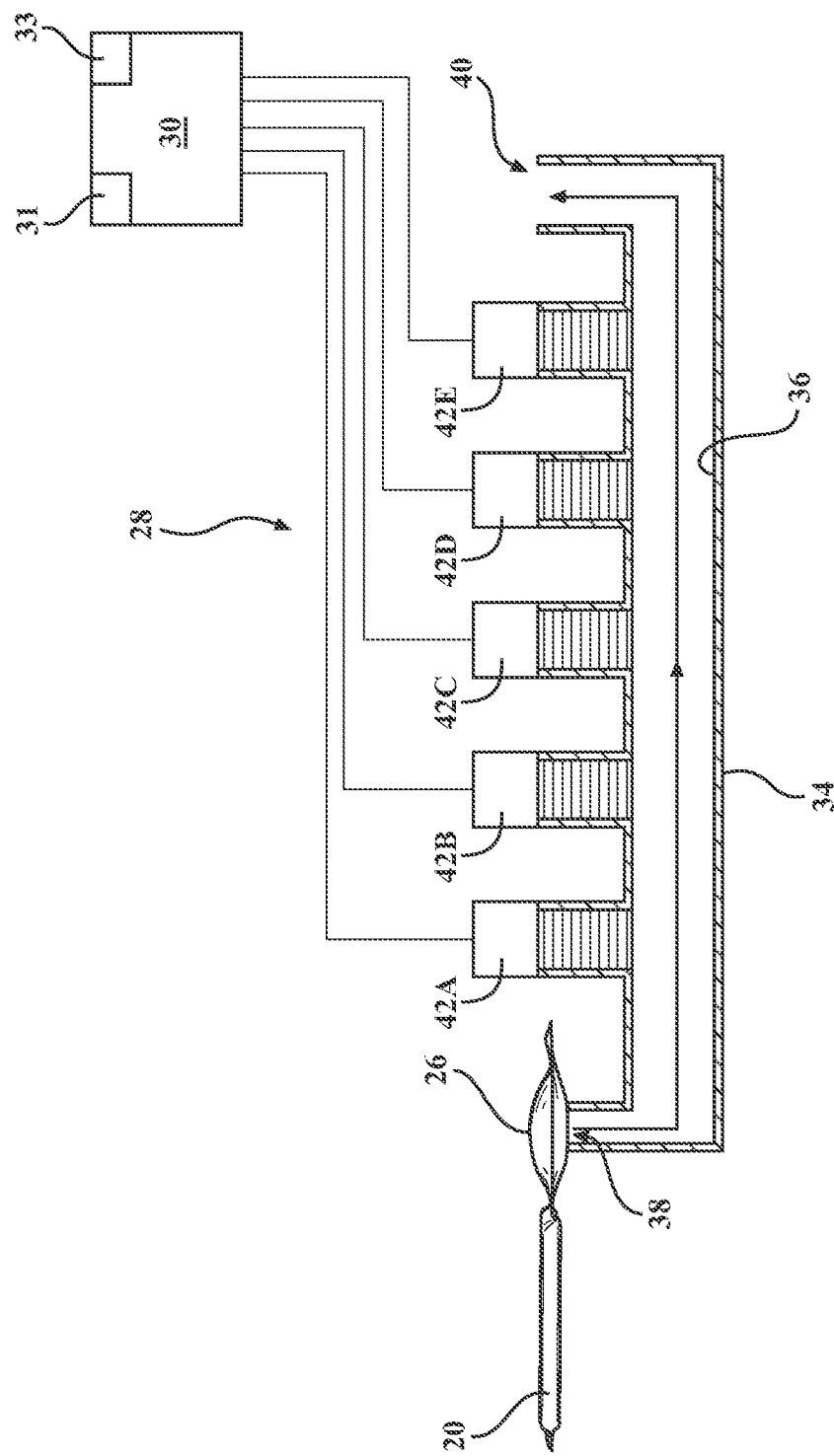
FIG. 3 is a schematic view of one example of a quality control system comprising a computational system, a manifold, and at least one sensor, and the battery cell of FIG. 2.

To this end, a quality control system 28 for analyzing the quality of the battery cell 20 is disclosed herein and shown in FIG. 3. The quality control system 28 comprises a computational system 30 comprising a processor 31 and a memory 33 comprising program instructions. The memory 33 may be further defined as a non-transitory computer-readable medium which includes, but is not limited to, random access memory (RAM), hard disk drive, and a flash drive. The quality control system 28 further comprises a manifold 34 defining a passageway 36 extending between an inlet port 38 configured to be in fluid communication with the gas pouch 26 for receiving the gas and an outlet port 40 in fluid communication with the inlet port 38 through the passageway 36 and configured to exhaust the gas from the manifold 34. The quality control system 28 further comprises at least one sensor 42 coupled to the manifold 34 and in fluid communication with the passageway 36, with the sensor 42 in electronic communication with the computational system 30, and with the sensor 42 arranged to measure a physical property of the gas removed from the gas pouch 26 and transmit a signal to the computational system 30 corresponding to the physical property of the gas. The computational system 30 is arranged to analyze the physical property of the gas with the processor 31 and access a threshold value corresponding to the physical property stored in the memory 33 to compare the physical property to the threshold value and assess a quality score for the battery cell 20.

The at least one sensor 42 may be further defined as a plurality of sensors 42 comprising at least a pressure sensor 42A configured to measure the pressure of the gas in the manifold 34 and a temperature sensor 42B configured to measure the temperature of the gas in the manifold 34. The pressure sensor 42A transmits the signal with the pressure of the gas to the computational system 30 and the temperature sensor 42B transmits the signal with the temperature of the gas to the computational system 30. The computational system 30 is arranged to analyze the pressure and temperature of the gas to determine a volume of the gas within the gas pouch 26, with the threshold value further defined as a volume threshold value and with the processor 31 arranged to compare the volume to the volume threshold value and assess the quality score for the battery cell 20. The processor 31 may determine the volume of the gas in accordance with the Ideal Gas Law:

$$PV=nRT$$

where P, V, and T are the pressure, volume and temperature, n is the amount of substance, and R is the ideal gas constant. The volume threshold value may be further defined as two volume threshold values, with one of the volume threshold values about 0.5 mL/Ah and the other one of the volume threshold values about 3 mL/Ah, in accordance with the example described above. In this context, the term "about" is known to those skilled in the art. Alternatively, the term "about" may be read to mean plus or minus 0.5 mL/Ah. The quality score may be further defined as a low-quality score when the volume is below 0.5 mL/Ah or above 3 mL/Ah. On the other hand, if the volume is between 0.5 mL/Ah and 3 mL/Ah, the processor 31 may assess a satisfactory quality score for the battery cell 20. Based upon the volume determined by the computational system 30 in comparison with the known thresholds, the computational system 30 will assess the quality score for the battery cell 20. Depending on the quality score, the battery cell 20 may continue through production, may be withdrawn from production for further quality assessment, or may be removed entirely from production (i.e., scrapped).

The plurality of sensors 42 may further comprise a gas detection sensor 42C-42E configured to measure the composition of the gas within the gas pouch 26 and wherein the gas detection sensor 42C-42E transmits the signal with the composition of the gas to the computational system 30. More specifically, in the example shown in the FIG. 3, the gas detection sensor 42C-42E is utilized in conjunction with the pressure and temperature sensors 42A, 42B. However, the gas detection sensor 42C-42E may be utilized independently. In this example, the threshold value is further defined as a composition threshold value and the processor 31 is arranged to compare the composition of the gas to the composition threshold value and assess the quality score for the battery cell 20. The composition threshold value may pertain the threshold molarity for a particular substance within the gas. In the examples herein, the quality score is further defined as a low-quality score when the composition of the gas is above the composition threshold value. However, in other examples not shown herein, the with the composition of the gas being below the threshold molarity may result in the low-quality score.

Figure 4:
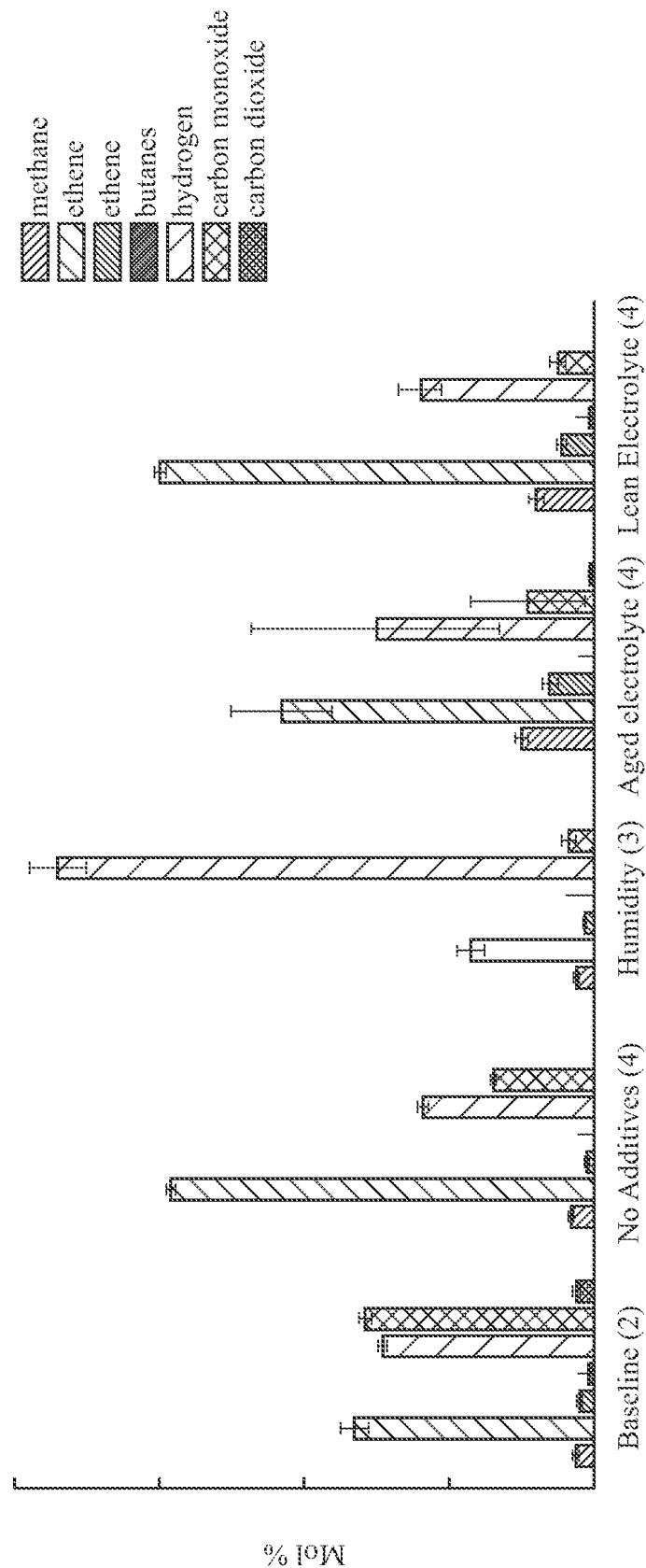
FIG. 4 is a bar graph showing the composition of substances within the gas of the battery cell.
Figure 5:
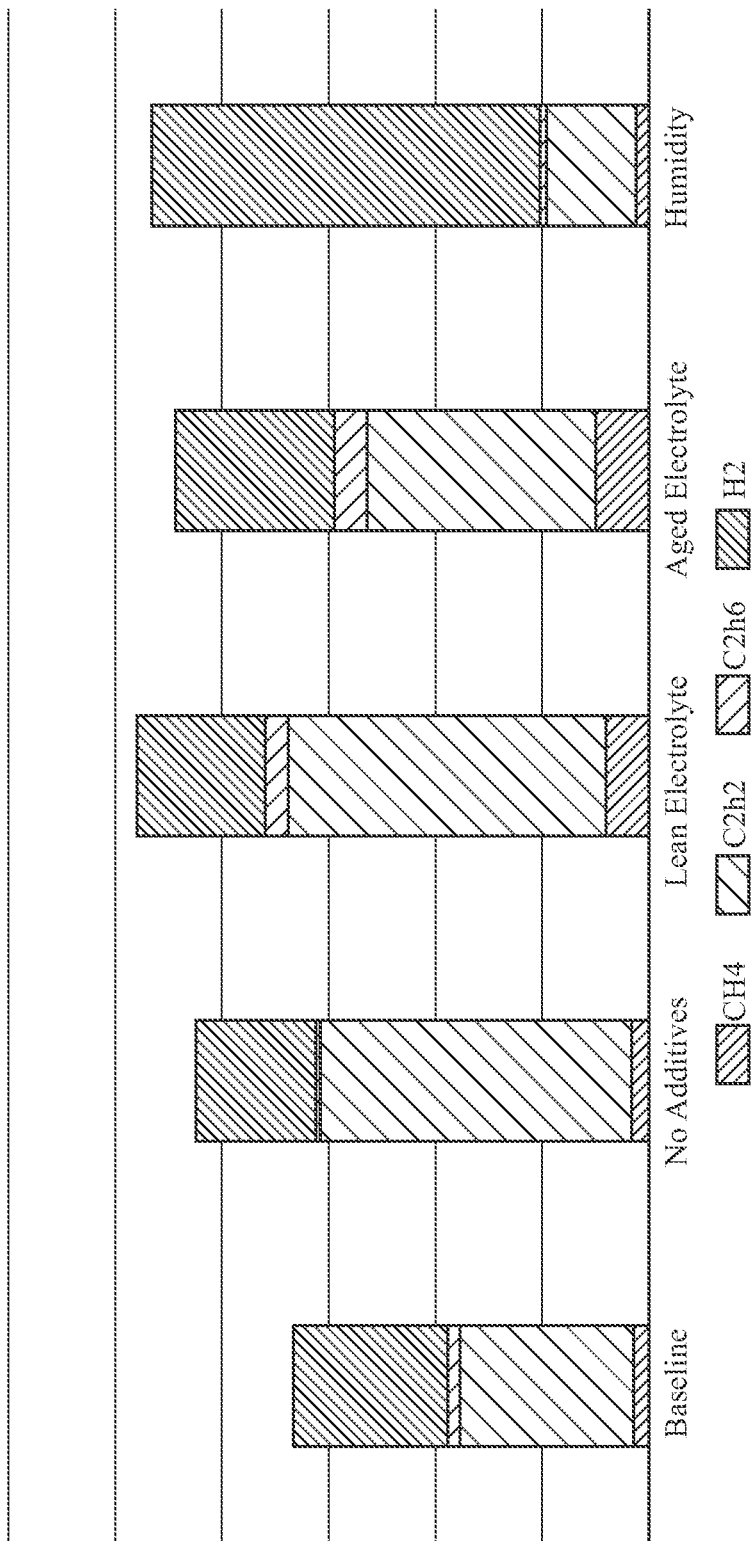
FIG. 5 is a bar graph showing the cumulative composition of the substances within the gas of the battery cell.

In this example, the plurality of sensors 42 comprises a plurality of the gas detection sensor 42C-42E. Each gas detection sensor 42C-42E is configured to measure the composition of a different substance within the gas. In the example shown herein, the gas detection sensor 42C-42E comprises one of a metal oxide sensor 42C, an oxygen and nitrogen oxide (O2/NOx) sensor 42D, and a hydrogen (H2) sensor 42E. These sensors facilitate the detection of at least nitrogen dioxide, hydrogen, carbon monoxide, methane, ammonia, ethene, ethane, ethanol, propane, iso-butane, and carbon dioxide. The processor 31 may individually identify the composition of the gas for each of the substances. The individual substances may be compared against individual composition threshold values for each of the substances, with the individual substances capable of the being assessed a quality score. Alternatively, the composition threshold value may be further defined as a cumulative composition threshold value. The processor 31 may be arranged to summate the compositions of the different substances within the gas into a cumulative composition, compare the cumulative composition of the gas to the cumulative composition threshold value, and assess the quality score for the battery cell 20. The bar graph shown in FIG. 4 show five examples of the composition of the individual substances being analyzed. The individual substances include methane, ethene, ethane, butane, hydrogen, carbon monoxide, and carbon dioxide. Each of the examples show a different scenario for the quality of a battery cell 20. Moving from left to right, the first group of seven bars show the composition of the substances in a baseline (good quality) battery cell. The second group of seven bars show the composition of the substances in a battery cell with no additives (low-quality). The third group of seven bars show the composition of the substances in a battery cell with humidity (low-quality). The fourth group of seven bars show the composition of the substances in a battery cell with aged electrolytes (low-quality). The fifth group of seven bars show the composition of the substances in a battery cell with lean electrolytes (low-quality). The individual composition of the substances is different in each scenario and distinctive to their particular quality scenario. Variations in the individual compositions can occur. To quickly identify a low-quality battery cell, the individual compositions in each scenario may be summated and compared to the cumulative composition threshold value (shown in graph in FIG. 5). The graph in FIG. 5 stacks the individual composition values shown in FIG. 4. The stacked bars (i.e., the cumulative composition) for the no additive, lean electrolyte, aged electrolyte, and humidity scenarios extend above the baseline, which represents the cumulative composition threshold value. If cumulative composition is greater than the cumulative composition threshold value, the battery cell is assessed a low-quality score.

The processor 31 may compare the quality score of the battery cell 20 from the volume of the gas to the quality score of the battery cell 20 from the composition of the gas and assess a global quality score for the battery cell 20. More specifically, the global quality score comprises an array of quality scores that when analyzed together provide an accurate assessment of the overall quality of the battery cell 20. In one example, the quality score of the volume and the quality score of the cumulative composition may be analyzed. If both quality scores show a low-quality battery cell 20, then the battery cell 20 is marked as low-quality. If both quality scores show a good-quality battery cell 20, then the battery cell 20 is marked as good-quality. If the quality scores are split (i.e., one low-quality and one good-quality), then a further analysis may be performed. For example, the difference between the threshold and analyzed values may be assessed to determine how poor of quality is the battery cell 20. An analysis of the individual compositions may also be performed to see what manufacturing scenario likely caused the low-quality assessment (i.e., no additives, lean electrolyte, aged electrolyte, and humidity).

Figure 6:
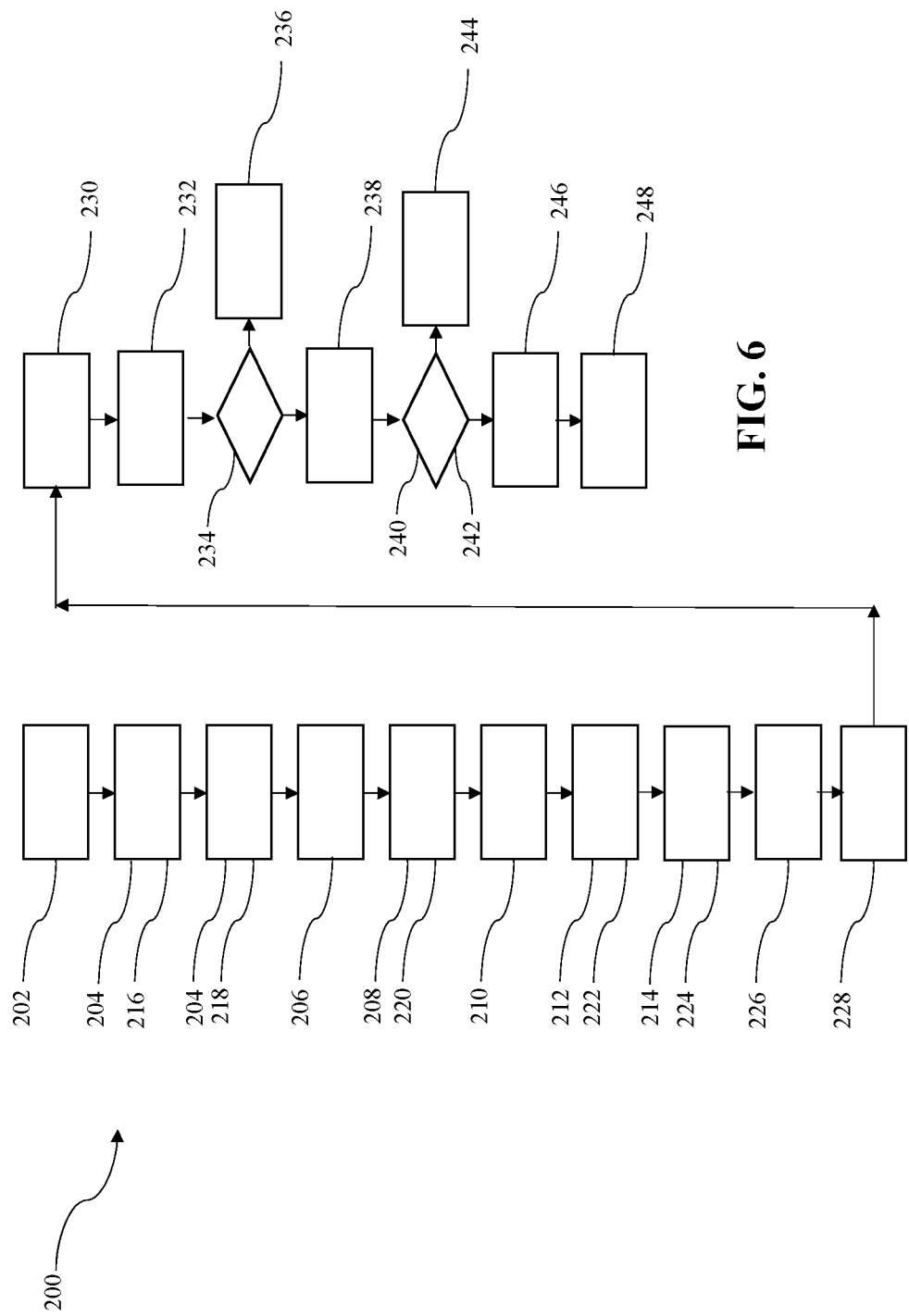
FIG. 6 is a flow chart of one example of a method of analyzing the quality of a battery cell with the quality control system.

A method 200 of analyzing the quality of the battery cell 20 with the quality control system 28 is also disclosed herein and shown in FIG. 6. The method comprises flowing the gas from the gas pouch 26 through the inlet port 38, through the passageway 36, across the at least one sensor 42, and through the outlet port 40 as shown in box 202, measuring the physical property of the gas with the at least one sensor 42 as shown in box 204, and transmitting the signal from the at least one sensor 42 to the processor 31 of the computational system 30 corresponding to the physical property of the gas as shown in box 206. The method further comprises analyzing the physical property of the gas with the processor 31 as shown in box 208, accessing the threshold value corresponding to the physical property stored in the memory 33 of the computational system 30 with the processor 31 as shown in box 210, comparing the physical property of the gas to the threshold value with the processor 31 as shown in box 212, and assessing the quality score for the battery cell 20 with the processor 31 as shown in box 214.

The at least one sensor 42 may be further defined as the plurality of sensors 42 comprising at least the pressure sensor 42A configured to measure the pressure of the gas in the manifold 34 and the temperature sensor 42B configured to measure the temperature of the gas in the manifold 34. Measuring the physical property of the gas with the at least one sensor 42 as shown in box 204 may be further defined as measuring the pressure of the gas within the manifold 34 with the pressure sensor 42A as shown in box 216 and measuring the temperature of the gas within the manifold 34 with the temperature sensor 42B as shown in box 218. Furthermore, analyzing the physical property of the gas with the computational system 30 as shown in box 208 may be further defined as analyzing the pressure and temperature of the gas and determining the volume of the gas within the gas pouch 26 with the processor 31 as shown in box 220.

The threshold value may be further defined as the volume threshold value, with comparing the physical property of the gas to the threshold value with the processor 31 as shown in box 212 further defined as comparing the volume of the gas to the volume threshold value as shown in box 222, and assessing the quality score for the battery cell 20 with the processor 31 as shown in box 214 further defined as assessing the quality score from the volume of the gas for the battery cell 20 as shown in box 224. The volume threshold value may be defined as two volume threshold values, with one of the volume threshold values about 0.5 mL/Ah and the other one of the volume threshold values about 3 mL/Ah and wherein the quality score is the low-quality score for the volume below 0.5 mL/Ah or above 3 mL/Ah.

The plurality of sensors 42 may further comprise the gas detection sensor 42C-42E and the method may further comprise measuring the composition of the gas within the gas pouch 26 with the gas detection sensor 42C-42E as shown in box 226 and transmitting the signal from the at least one sensor 42 to the processor 31 of the computational system 30 corresponding to the composition of the gas as shown in box 228. The threshold value may be further defined as the composition threshold value and the method may further comprise comparing the composition of the gas to the composition threshold value as shown in box 230 and assessing the quality score from the composition of the gas for the battery cell 20 as shown in box 232. The method may further comprise assessing the global quality score from the quality score of the battery cell 20 from the volume of the gas and the quality score of the battery cell 20 from the composition of the gas as shown in box 234.

The method 200 may further comprise continuing production of the battery cell 20 as shown in box 236. The method 200 may further comprise removing the battery cell 20 from production based upon the quality score as shown in box 238. More specifically, if the computational system 30 assesses the quality score and the quality score is indicative of a low-quality battery cell 20, the battery cell 20 may be removed from production. If the battery cell 20 is removed from production, the method 200 may further comprise performing additional quality review of the battery cell 20 as shown box 240. In one example, performing additional quality review of the battery cell 20 is further defined as performing gas chromatography on the gas within the gas pouch 26 as shown in box 242. More specifically, the gas within the gas pouch 26 is removed from the gas pouch 26 and passed through a gas chromatograph. Gas chromatography is the process of separating compounds in gas disposed within the gas pouch 26, allowing for a thorough analysis of the composition of the gas. The composition of the gas in the low-quality battery cell 20 can be compared to a known composition found in a healthy battery cell. The deviations in the composition may be used to determine the root cause of the low-quality battery cell 20 (e.g., no additives, lean electrolyte, aged electrolyte, humidity, etc.).

The method 200 may further comprise reintroducing the battery cell 20 into production as shown in box 244. More specifically, if after performing the additional quality review, the battery cell 20 is found to have a quality that falls within a desired specification, the battery cell 20 may be placed back into production and sold individually, as part of the battery pack, or in any other configuration. On the other hand, the method 200 may further comprise scrapping the battery cell 20 as shown in box 246 (i.e., permanently removing the battery cell 20 from production). The battery cell 20 may be disassembled and components may be utilized for recycling. Furthermore, the method 200 may further comprise altering the production of the battery cell 20 as shown in box 248. More specifically, if the root cause of the low-quality battery cell 20 may be ascertained, the production of the battery cell 20 may be adjusted to ensure the future production of battery cells 20 that fall within desired quality specifications. In one example, altering the production of the battery cell 20 is further defined as providing instructions for adaptive formation charge parameters. Adaptive formation charge parameters refer to performing corrective action to the cell formation process. More specifically, data from the cell formation process (such as voltage, current, pressure and temperature versus time) is monitored in real time and (if necessary) corrective actions on the formation schedule could be implemented to ensure desired SEI formation based upon feedback from the comprehensive quality check. Corrective action may include the processor of the computational system (or another computational system within a network) instructing a power supply to apply a corrected constant current or hold a corrected first and/or second voltage limit for a subsequent battery cell 20 during the cell formation process. The computational system may also instruct a temperature control module to correct the ambient temperature of the subsequent battery cell 20 (e.g., with a heater and/or an air conditioner) during the cell formation process. The data from the cell formation process, along with the analysis result from the comprehensive quality check and modified actions to the cell formation process may be archived in a networked repository. Information from this repository could be used to further analyze cell quality down the manufacturing line.

Accordingly, the quality control system 28 and the corresponding method 200 of analyzing the quality of a battery cell 20 with a quality control system 28 offer several advantages. Checking the quality of the battery cell 20 after the cell formation process reduces the need to perform lengthy inventory holds and open circuit voltage monitoring as currently practiced, which increases manufacturing throughput. Furthermore, analysis of the gas produced by the cell formation process provides data that be used to assess the quality of the battery cell 20 and the oxidation-reduction therein, without destroying a battery cell 20 to analyze the SEI on the anode.

The description of the present disclosure is merely exemplary in nature and variations that do not depart from the general sense of the present disclosure are intended to be within the scope of the present disclosure. Such variations are not to be regarded as a departure from the spirit and scope of the present disclosure.

What is claimed is:

1. A quality control system for analyzing the quality of a battery cell, with the battery cell defining a gas pouch configured to be filled with a gas formed during a cell formation process of the battery cell, the quality control system comprising:
   a computational system comprising a processor and a memory; and
   a manifold defining a passageway extending between an inlet port configured to be in fluid communication with the gas pouch for receiving the gas and an outlet port in fluid communication with the inlet port through the passageway and configured to exhaust the gas from the manifold; and
   at least one sensor coupled to the manifold and in fluid communication with the passageway, with the sensor in electronic communication with the computational system, and with the sensor arranged to measure a physical property of the gas removed from the gas pouch and transmit a signal to the computational system corresponding to the physical property of the gas;
   wherein the computational system is arranged to analyze the physical property of the gas with the processor and access a threshold value corresponding to the physical property stored in the memory to compare the physical property to the threshold value and assess a quality score for the battery cell.

2. The quality control system of claim 1 wherein the at least one sensor is further defined as a plurality of sensors comprising at least a pressure sensor configured to measure the pressure of the gas in the manifold and a temperature sensor configured to measure the temperature of the gas in the manifold, wherein the pressure sensor transmits the signal with the pressure of the gas to the computational system and the temperature sensor transmits the signal with the temperature of the gas to the computational system.

3. The quality control system of claim 2 wherein the computational system is arranged to analyze the pressure and temperature of the gas to determine a volume of the gas within the gas pouch, with the threshold value further defined as a volume threshold value and with the processor arranged to compare the volume to the volume threshold value and assess the quality score for the battery cell.

4. The quality control system of claim 3 wherein the volume threshold value is further defined as two volume threshold values, with one of the volume threshold values about 0.5 mL/Ah and the other one of the volume threshold values about 3 mL/Ah, with the quality score further defined as a low-quality score when the volume is below 0.5 mL/Ah or above 3 mL/Ah.

5. The quality control system of claim 3 wherein the plurality of sensors further comprises a gas detection sensor configured to measure the composition of the gas within the gas pouch and wherein the gas detection sensor transmits the signal with the composition of the gas to the computational system.

6. The quality control system of claim 5 wherein the threshold value is further defined as a composition threshold value and with the processor arranged to compare the composition of the gas to the composition threshold value and assess the quality score for the battery cell.

7. The quality control system of claim 6 wherein the quality score further defined as a low-quality score when the composition of the gas is above the composition threshold value.

8. The quality control system of claim 6 wherein the plurality of sensors comprises a plurality of the gas detection sensor, with each gas detection sensor configured to measure the composition of a different substance within the gas.

9. The quality control system of claim 8 wherein the composition threshold value is further defined as a cumulative composition threshold value and wherein the processor is arranged to summate the compositions of the different substances within the gas into a cumulative composition, compare the cumulative composition of the gas to the cumulative composition threshold value, and assess the quality score for the battery cell.

10. The quality control system of claim 5 wherein the gas detection sensor comprises one of a metal oxide sensor, an oxygen and nitrogen oxide ($O_2/NO_x$) sensor, and a hydrogen ($H_2$) sensor.

11. The quality control system of claim 6 wherein the processor compares the quality score of the battery cell from the volume of the gas to the quality score of the battery cell from the composition of the gas and assess a global quality score for the battery cell.

12. A method of analyzing the quality of a battery cell with a quality control system, with the battery cell defining a gas pouch filled with a gas formed during a cell formation process of the battery cell, and with the quality control system comprising a computational system, a manifold defining a passageway extending between an inlet port configured to be in fluid communication with the gas pouch for receiving the gas and an outlet port in fluid communication with the inlet port through the passageway and configured to exhaust the gas from the manifold, and at least one sensor coupled to the manifold and in fluid communication with the passageway, with the sensor in electronic communication with the computational system, the method comprising:
   flowing the gas from the gas pouch through the inlet port, through the passageway, across the at least one sensor, and through the outlet port;
   measuring a physical property of the gas with the at least one sensor;
   transmitting a signal from the at least one sensor to a processor of the computational system corresponding to the physical property of the gas;
   analyzing the physical property of the gas with the processor;
   accessing a threshold value corresponding to the physical property stored in a memory of the computational system with the processor;

comparing the physical property of the gas to the threshold value with the processor; and assessing a quality score for the battery cell with the processor.

13. The method as set forth in claim 12 wherein the at least one sensor is further defined as a plurality of sensors comprising at least a pressure sensor configured to measure the pressure of the gas in the manifold and a temperature sensor configured to measure the temperature of the gas in the manifold and wherein measuring the physical property of the gas with the at least one sensor is further defined as measuring the pressure of the gas within the manifold with the pressure sensor and measuring the temperature of the gas within the manifold with the temperature sensor.

14. The method as set forth in claim 13 wherein analyzing the physical property of the gas with the computational system is further defined as analyzing the pressure and temperature of the gas and determining a volume of the gas within the gas pouch with the processor.

15. The method as set forth in claim 14 wherein the threshold value is further defined as a volume threshold value, with comparing the physical property of the gas to the threshold value with the processor further defined as comparing the volume of the gas to the volume threshold value and assessing the quality score for the battery cell with the processor further defined as assessing the quality score from the volume of the gas for the battery cell.

16. The method as set forth in claim 15 wherein the volume threshold value is defined as two volume threshold values, with one of the volume threshold values about 0.5 mL/Ah and the other one of the volume threshold values about 3 mL/Ah and wherein the quality score is a low-quality score for the volume below 0.5 mL/Ah or above 3 mL/Ah.

17. The method as set forth in claim 15 wherein the plurality of sensors further comprises a gas detection sensor and further comprising measuring the composition of the gas within the gas pouch with the gas detection sensor and transmitting a signal from the at least one sensor to the processor of the computational system corresponding to the composition of the gas.

18. The method as set forth in claim 17 wherein the threshold value is further defined as a composition threshold value and further comprising comparing the composition of the gas to the composition threshold value and assessing a quality score from the composition of the gas for the battery cell.

19. The method as set forth in claim 17 further comprising assessing a global quality score from the quality score of the battery cell from the volume of the gas and the quality score of the battery cell from the composition of the gas.

20. A method of analyzing the quality of a battery cell with a quality control system, with the battery cell defining a gas pouch filled with a gas formed during a cell formation process of the battery cell, and with the quality control system comprising a computational system, a manifold defining a passageway extending between an inlet port and an outlet port, and a plurality of sensors coupled to the manifold and in fluid communication with the passageway, with the sensors in electronic communication with the computational system and with the plurality of sensors comprising a pressure sensor, a temperature sensor, and a gas detection sensor, the method comprising:

flowing the gas from the gas pouch through the inlet port, through the passageway, across the sensors, and through the outlet port;

measuring the pressure of the gas within the manifold with the pressure sensor;

measuring the temperature of the gas within the manifold with the temperature sensor;

transmitting a signal from the at least one sensor to a processor of the computational system corresponding to the physical property of the gas;

analyzing the pressure and temperature of the gas and determining a volume of the gas within the gas pouch with the processor, accessing a volume threshold value, corresponding to the volume determined from the pressure and the temperature, stored in a memory of the computational system with the processor;

comparing the volume of the gas to the volume threshold value with the processor;

assessing a quality score from the volume of the gas for the battery cell with the processor;

measuring the composition of the gas within the gas pouch with the gas detection sensor;

transmitting a signal from the at least one sensor to the processor of the computational system corresponding to the composition of the gas;

accessing a composition threshold value stored in a memory of the computational system with the processor;

comparing the composition of the gas to the composition threshold value with the processor;

assessing a quality score from the composition of the gas for the battery cell with the processor; and assessing a global quality score from the quality score of the battery cell from the volume of the gas and the quality score of the battery cell from the composition of the gas.

* * * * *